United States Patent
Singh et al.

(10) Patent No.: US 9,642,815 B2
(45) Date of Patent: May 9, 2017

(54) BIOCOMPATIBLE GRAPHENE QUANTUM DOTS FOR DRUG DELIVERY AND BIOIMAGING APPLICATIONS

(71) Applicant: Council of Scientific and Industrial Research, New Delhi (IN)

(72) Inventors: Neetu Singh, Pune (IN); Anil Chandra, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/033,513

(22) PCT Filed: Nov. 3, 2014

(86) PCT No.: PCT/IN2014/000705
§ 371 (c)(1),
(2) Date: Apr. 29, 2016

(87) PCT Pub. No.: WO2015/063799
PCT Pub. Date: May 7, 2015

(65) Prior Publication Data
US 2016/0256403 A1    Sep. 8, 2016

(30) Foreign Application Priority Data
Nov. 1, 2013 (IN) .......................... 3244/DEL/2013

(51) Int. Cl.
*A61K 9/00* (2006.01)
*A61K 9/51* (2006.01)
(Continued)

(52) U.S. Cl.
CPC ........ *A61K 9/5146* (2013.01); *A61K 49/0067* (2013.01); *B82Y 5/00* (2013.01);
(Continued)

(58) Field of Classification Search
CPC .................................................. A61K 9/5146
See application file for complete search history.

(56) References Cited

U.S. PATENT DOCUMENTS

2012/0068154 A1* 3/2012 Hwang ................ H01L 51/502
257/13
2013/0175182 A1 7/2013 Shinde et al.

FOREIGN PATENT DOCUMENTS

WO   WO-2015/063799   5/2015

OTHER PUBLICATIONS

Akhavan, Omid, et al., "Nontoxic concentrations of PEGylated graphene nanoribbons for selective", *J. Mater. Chem.*, 22(38), (2012), 20626-20633.
(Continued)

*Primary Examiner* — Paul Dickinson
(74) *Attorney, Agent, or Firm* — Schwegman Lundberg & Woessner, P.A.

(57) ABSTRACT

In this work we have targeted two aspects of GQDs, Size and ROS to reduce their cytotoxicity. Small size can damage cell organelles and production of ROS (reactive oxygen species) can hamper cell machinery in multiple ways. We have shown that cytotoxicity can be significantly reduced by embedding GQDs inside the PEG matrix rather than creating a thin shell around each GQD. Thin PEG shell around GQD can control ROS production but cannot circumvent the toxicity due to small size. Thus it was essential to solve both the issues. We have used a simple electrochemical method (12 h at room temperature) for synthesizing GQDs and embedded them in PEG matrix via a simple one step hydrothermal reaction (24 h at 160° C.) involving only GQDs, PEG, and deionized water. The P-GQDs formed after hydrothermal reaction show nanoparticles of diameter of ~80-100 nm containing GQDs entrapped in PEG matrix. MTT assay showed significant 60% cells viability at a very (Continued)

high concentration of 5.5 mg/mL of P-GQDs compared to 10-15% viability for C-GQD and H-GQD. ROS production by P-GQDs was least compared to C-GQD and H-GQD in cell free and intracellular ROS assay suggesting involvement of ROS in cytotoxicity. In this work we have solved the issue of cytotoxicity due to 'small size' and 'ROS generation' without compromising with fluorescence properties of GQDs. P-GQDs was used for bioimaging and drug delivery in HeLa cells. In short we can obtain biocompatible P-GQDs in very short span of time with minimal use of hazardous chemicals and simple methodology.

4 Claims, 10 Drawing Sheets

(51) Int. Cl.
| | |
|---|---|
| B82Y 5/00 | (2011.01) |
| A61K 49/00 | (2006.01) |
| G01N 33/50 | (2006.01) |
| C01B 31/04 | (2006.01) |
| C25B 1/00 | (2006.01) |
| C25F 3/02 | (2006.01) |
| B82Y 40/00 | (2011.01) |
| B82Y 15/00 | (2011.01) |
| B82Y 30/00 | (2011.01) |

(52) U.S. Cl.
CPC ............ *C01B 31/0446* (2013.01); *C25B 1/00* (2013.01); *C25F 3/02* (2013.01); *G01N 33/50* (2013.01); *B82Y 15/00* (2013.01); *B82Y 30/00* (2013.01); *B82Y 40/00* (2013.01); *Y10S 977/774* (2013.01); *Y10S 977/788* (2013.01); *Y10S 977/888* (2013.01); *Y10S 977/90* (2013.01); *Y10S 977/906* (2013.01); *Y10S 977/927* (2013.01)

(56) References Cited

OTHER PUBLICATIONS

Bhunia, Susanta, et al., "Carbon Nanoparticle-based Fluorescent Bioimaging Probes", *Scientific Reports*, 3: 1473, (2013), 1-7.

Dong, Yongqiang, et al., "One-step and high yield simultaneous preparation of single- and multi-layer graphene quantum dots from CX-72 carbon black", *J. Mater. Chem.*, 22, (2012), 8764-8766.

Kairdolf, Brad A., et al., "Semiconductor Quantum Dots for Bioimaging and Biodiagnostic Applications", *Annual Review of Analytical Chemistry*, vol. 6, (2013), 143-162.

Lay, Chee Leng, et al., "Delivery of paclitaxel by physically loading onto poly(ethylene glycol) (PEG)-graft-carbonn anotubes for potent cancer thrapeutics", *Nanotechnology*, 21, 065101, (2010), 1-10.

Liu, Zhuang, et al., "PEGylated Nanographene Oxide for Delivery of Water-Insoluble Cancer Drugs", *J. Am. Chem. Soc.*, 130(33), (2008), 10876-10877.

Pan, Dengyu, et al., "Hydrothermal Route for Cutting Graphene Sheets into Blue-Luminescent Graphene Quantum Dots", *Adv. Mater.*, 22, (2010), 734-738.

Peng, Juan, et al., "Graphene Quantum Dots Derived from Carbon Fibers", *Nano Lett.*, 12(2), (2012), 844-849.

Pu, Yunqiao, et al., "Assessing the molecular structure basis for biomass recalcitrance during dilute acid and hydrothermal pretreatments", *Biotechnology for Biofuels*, 6:15, (2013), 13 pgs.

Shen, Jianhua, et al., "One-pot hydrothermal synthesis of graphene quantum dots surface-passivated by polyethylene glycol and their photoelectric conversion under near-infrared lightw", *New J. Chem.*, 36, (2012), 97-101.

Shinde, Dhanraj B., et al., "Electrochemical Preparation of Luminescent Graphene Quantum Dots from Multiwalled Carbon Nanotubes", *Chem. Eur. J.*, 18(39), (2012), 12522-12528.

Zhang, Xiaoyong, et al., "Size tunable fluorescent nano-graphite oxides: preparation and cell imaging applications", *Phys. Chem. Chem. Phys.*, 15(43), (2013), 19013-19018.

Zhu, Shoujun, et al., "Strongly green-photoluminescent graphene quantum dots for bioimaging applications", *Chem. Commun.*, 47, (2011), 6858-6860.

"International Application No. PCT/IN2014/000705, International Search Report and Written Opinion mailed Mar. 12, 2015", (Mar. 12, 2015), 8 pgs.

Berlin, Jacob M., et al., "Effective Drug Delivery, in vitro and in vivo, by Carbon-Based Nanovectors Non-Covalently Loaded With Unmodified Paclitaxel", ACS Nano. Aug. 24, 2010; 4(8): 4621-4636, (Aug. 24, 2010), 4621-4636.

Shinde, Dhanraj B., et al., "Electrochemical Preparation of Luminescent Graphene Quantum Dots from Multi-Walled Carbon Nanotubes", Chemistry—A European Journal, vol. 18, No. 39, Sep. 24, 2012, (Sep. 24, 2012), 12522-12528.

\* cited by examiner

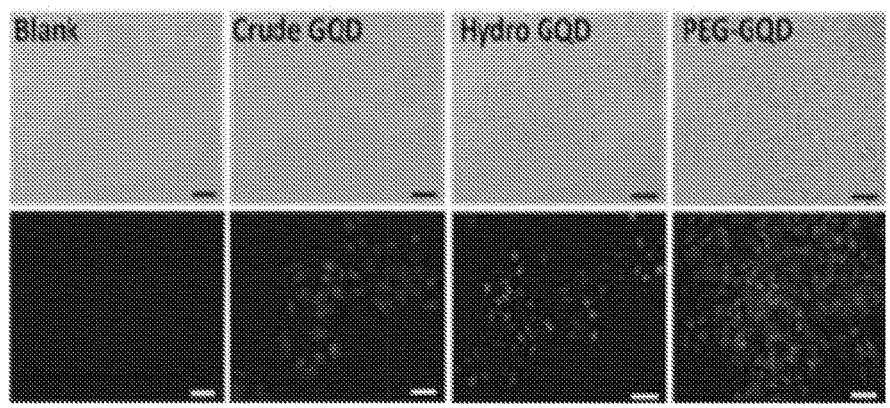
FIG. 6
FIG. 7A
FIG. 7B
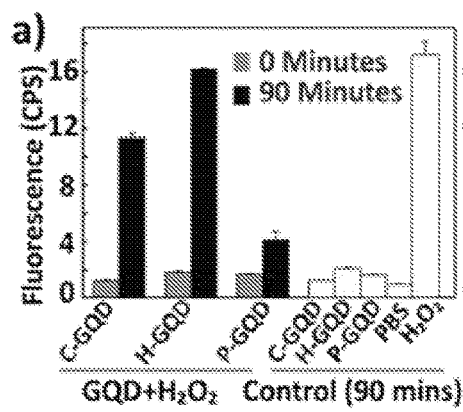
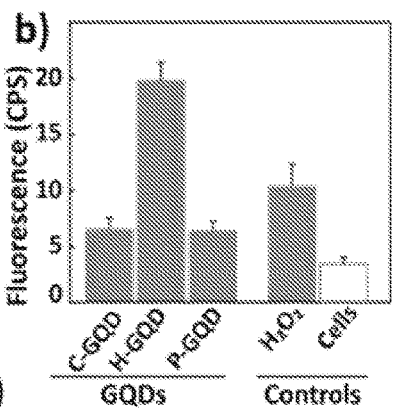
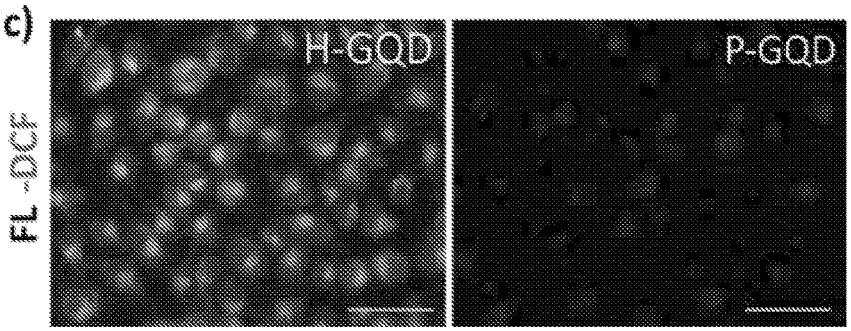
FIG. 7C

FIG. 8A  FIG. 8B  FIG. 8C
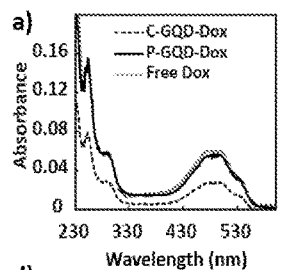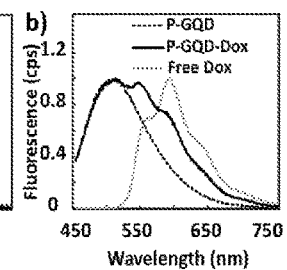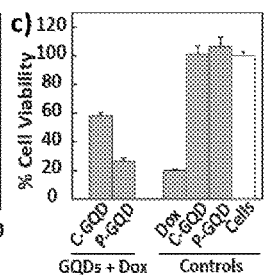
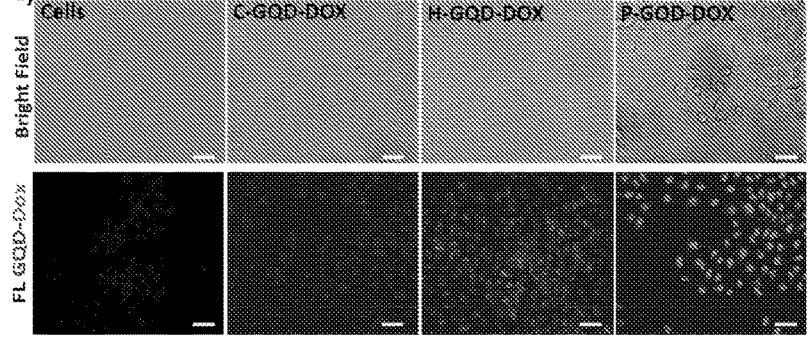
FIG. 8D
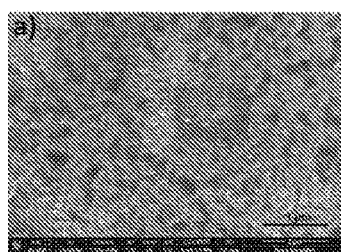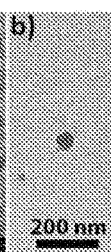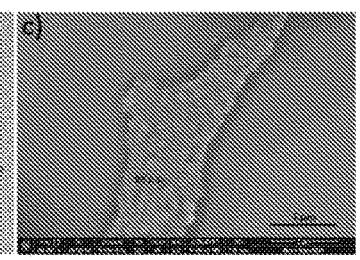
FIG. 9A  FIG. 9B  FIG. 9C

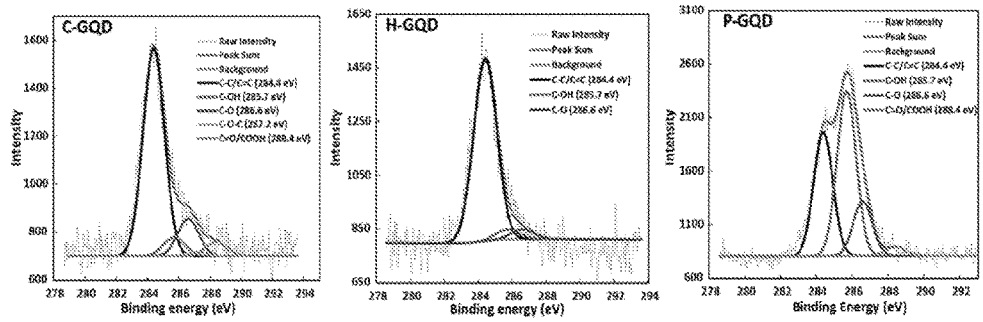
FIG. 12
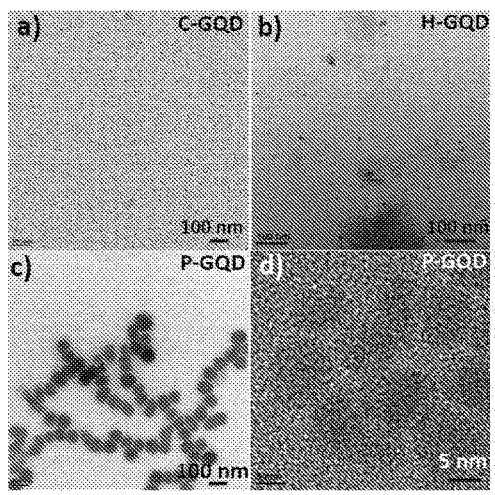
FIG. 13A   FIG. 13B
FIG. 13C   FIG. 13D
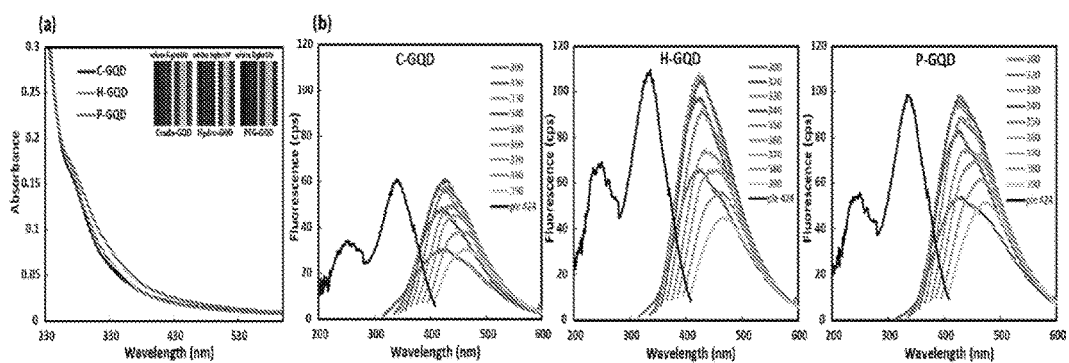
FIG. 14A   FIG. 14B FIG. 15A
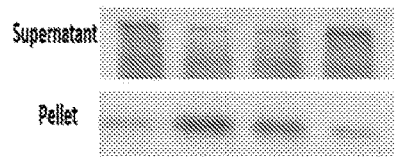
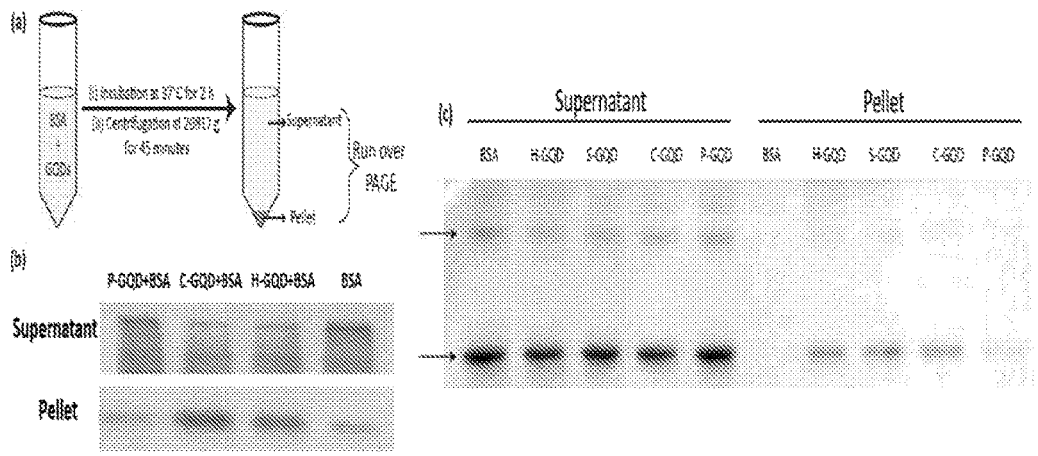
FIG. 15B FIG. 15C
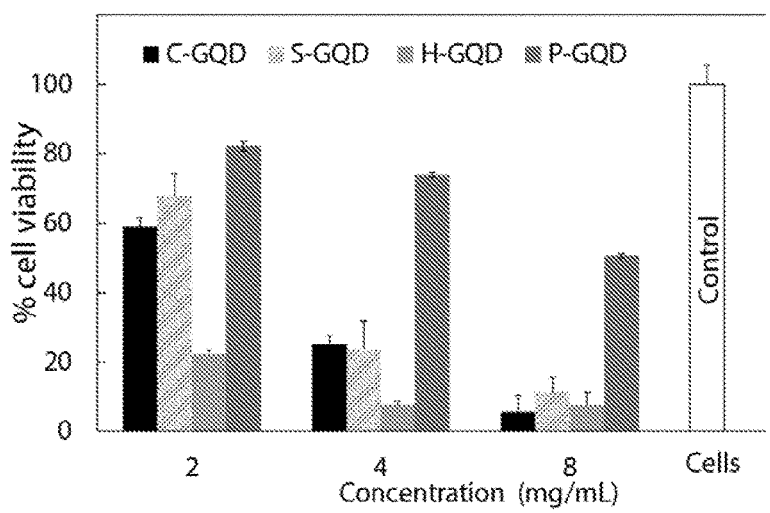
FIG. 16

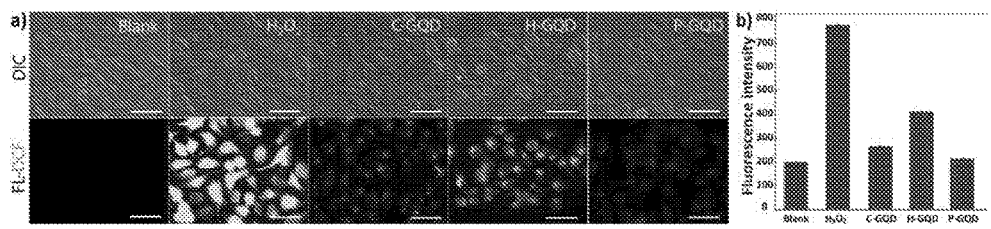
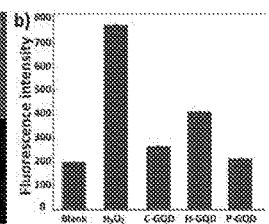
FIG. 19A  FIG. 19B
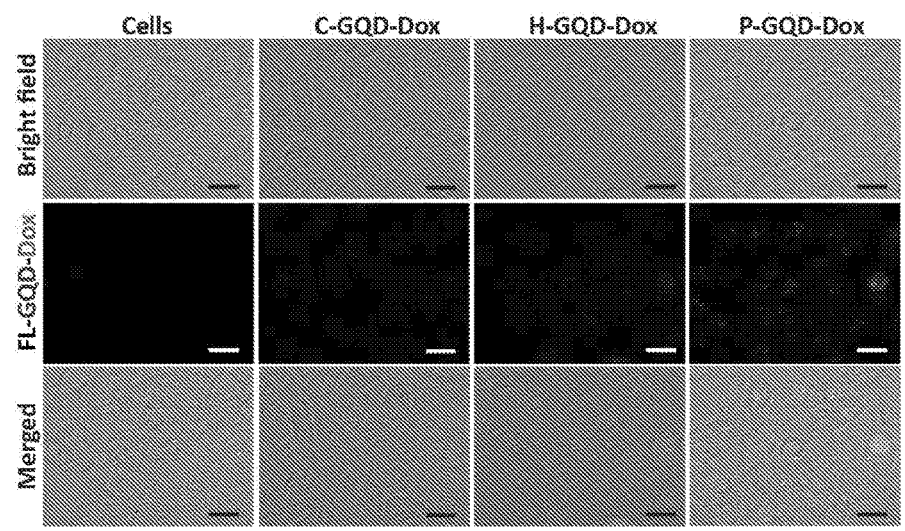
FIG. 20

US 9,642,815 B2

BIOCOMPATIBLE GRAPHENE QUANTUM DOTS FOR DRUG DELIVERY AND BIOIMAGING APPLICATIONS

PRIORITY CLAIM TO RELATED APPLICATIONS

This application is a U.S. national stage application filed under 35 U.S.C. §371 from International Application Serial No. PCT/IN2014/000705, which was filed 3 Nov. 2014, and published as WO2015/063799 on 7 May 2015, and which claims priority to India Application No. 3244/DEL/2013, filed 1 Nov. 2013, which applications and publication are incorporated by reference as if reproduced herein and made a part hereof in their entirety, and the benefit of priority of each of which is claimed herein

TECHNICAL FIELD OF THE INVENTION

The present invention relates to a biocompatible composition comprising Fluorescent Graphene Quantum Dots (GQDs) embedded in a polymer matrix of polyethylene glycol (PEG) with particle size ranging from 80-100 nm. Particularly, present invention provides a simple process for the preparation of said composition comprising Fluorescent Graphene Quantum Dots (GQDs) embedded in a polymer matrix of polyethylene glycol (PEG) (PEG-GQDs). The cytotoxicity of the instant PEG-GQD composition is reduced, thus making it convenient for application in drug delivery, bioimaging and other biomedical applications.

BACKGROUND AND PRIOR ART OF THE INVENTION

A quantum dot is a semiconductor nanostructure that confines the motion of conduction band electrons, valence band holes, or excitons in all three spatial directions. Quantum dots (QDs) are traditionally chalcogenides (selenides or sulfides) of metals like cadmium or zinc (CdSe or ZnS), which range from 2 to 10 nanometers in diameter.

QDs have unique optical and electronic properties such as size-tunable light emission, narrow and symmetric emission spectra, and broad absorption spectra that enable simultaneous excitation of multiple fluorescence. Moreover, QDs are resistant to photo bleaching than organic dyes and fluorescent proteins. These properties are well suited for dynamic imaging at the single-molecule level and for multiplexed biomedical diagnostics at ultrahigh sensitivity.

However, for in vivo and clinical imaging, the potential toxicity of QDs remains a major concern. The toxic nature of cadmium-containing QDs is no longer a factor for in vitro diagnostics, since emergent use of fluorescent QDs for molecular diagnostics and pathology is an important and clinically relevant application for semiconductor QDs. (Kairdolf. B. et al., *Annual Rev. of Analytical Chem. Vol. 6*: 143-162.)

In prevalent practice, the use of carbon nanoparticles in synthesis of quantum dots, have emerged as a new class of quantum dot-like fluorescent nanomaterials. Carbon nanoparticles are used since their particle size can be controlled between 3-20 nm. Carbon atoms linked in hexagonal shapes, wherein each carbon atom is covalently bonded to three other carbon atoms to form graphene sheets. Graphene has the same structure of carbon atoms linked in hexagonal shapes to form carbon nanotubes, but graphene is flat rather than cylindrical.

Graphene quantum dots (GQDs) are used as fluorophores for bioimaging, owing to their physicochemical properties including tunable photoluminescence, excellent photostability, and biocompatibility. GQDs usually less than 50 nm in size have been reported to have excellent fluorescent properties. Due to luminescence stability, nanosecond lifetime, biocompatibility, low toxicity, and high water solubility, GQDs are demonstrated to be excellent probes for high contrast bioimaging and bio sensing applications.

References may be made to prior art documents for methods of synthesizing GQDs using electrochemical processes, hydrothermal methods and the modified Hummers process for graphene oxide synthesis and cytotoxicity assays to determine the cellular uptake of the resultant GQDs formed by these processes.

US patent publication, US 2013/0175182 provides a process for the transformation of single walled, double walled or multi walled carbon nanotubes to nanoribbons composed of few layers of graphene by a two-step electrochemical process. The process involves oxidizing dispersed carbon nanotubes (CNT) to obtain CNT oxide and further reducing it to form graphene layers.

In research publication, *Chem. Commun*, 2011, 6858-6860, Zhu et al, describe a method of GQD preparation wherein modified Hummers method is used for graphene oxide synthesis and hydrothermal method for GQD synthesis to obtain GQDs of particle size of 5.3 nm. At concentrations of 2.6 mg/ml, cell viability of 80% is observed.

Further Jianhua Shen et al. in *New J. Chem.*, 2012, 36, 97-101 reported one-pot hydrothermal reaction for preparation of graphene quantum dots surface-passivated by polyethylene glycol (GQDs-PEG) and their photoelectric conversion under near-infrared light, using small graphene oxide (GO) sheets and polyethylene glycol (PEG) as starting materials.

Juan Peng et al. (*Nano Lett.*, 2012, 12 (2), pp 844-49) describes the acid treatment and chemical exfoliation of carbon fibers, to provide GQDs in the size range of 1-4 nm. The publication provides that the GQDs derived have no toxicity at concentrations of 0.05 mg/ml. However, the cytotoxicity of GQDs at higher levels is unaccounted.

Chang Ming Li et al., (*J. Mater. Chem.*, 2012, 8764-66) provide a method to develop graphene quantum dots (GQDs) from XC-72 carbon black by chemical oxidation, however toxicity assays confirm maximum cell viability at concentrations of 0.1 mg/ml.

The toxicity of GQDs is attributed to their size, since small sized GQDs interact with various proteins and organelles inside the cell and disrupt cellular processes. Another reason for the toxicity is their ability to generate more reactive oxygen species (ROS). Polymers, especially PEG coating has been used in the literature to decrease the toxicity of GQDs. However, even after polymer coating the cell viability at higher concentrations (>1 mg/ml) is low. Probably because even though the ROS production is lowered by the polymer shell coating, the size of the GQDs after coating still remains small (sub 50 nm) and are still in the size range that can interact with intracellular proteins and organelles.

In the following research publications, references may be made to PEGylation of carbon nanoparticles and the cell viability determined at concentrations of 1 mg/ml or lesser than that.

Bhunia et al., (*Scientific Reports*, 2013, 3:1473) describe carbon nanoparticles (FCN) which are polymer coated with PEG and the dosage dependent cellular toxicity of these fluorescent nanoparticles. At 1 mg/ml concentration of the FCN-PEG composition, 55-60% cell viability is observed.

Zhuang Liu et al., (*J. Am. Chem. Soc.*, 2008, 130 (33), pp 10876-10877) describe pegylated nano-graphene oxide (NGO-PEG) of size 5-50 nm for delivery of water insoluble cancer drugs produced by Hummers method.

Omid Akhavan et al., (*J. Material. Chem.*, 2012, *Vol.* 22, 20626-33) describes nontoxic concentrations of pegylated graphene nanoribbons for selective cancer cell imaging and photothermal therapy. At concentrations of 1 mg/ml of the composition. 28% cell viability was obtained.

Further Lay C L et al. (*Nanotechnology.* 2010 Feb. 10; 21(6):065101) reports delivery of paclitaxel by physically loading onto poly (ethylene glycol) (PEG)-graft-carbon nanotubes for potent cancer therapeutics.

Toxicity assays of GQDs synthesized by methods of the above prior arts report minimum cell viability at GQDs concentrations of 1 mg/ml, and lesser than that, thus posing limitations in cellular imaging applications. However, to realize biomedical applications of GQDs, low toxicity of the GQDS at higher concentrations is desired for cellular imaging.

With a view to provide graphene quantum dots (GQDs) with decreased cytotoxicity levels at higher concentrations i.e. greater than 1 mg/ml, the present inventors have provided a biocompatible composition of one or more graphene quantum dots (GQDs) in a nanosized polymer matrix of polyethylene glycol which is larger compared to small sized GQDs as observed in the prior art. The PEG matrix aids in reducing the reactive oxygen radicals (ROS) generated by the GQD surface while keeping the small GQDs inside the matrix; thus, also reducing their undesirable interactions with cellular proteins and organelles.

SUMMARY OF THE INVENTION

Accordingly, present invention provides biocompatible composition with reduced cytotoxicity comprising graphene quantum dots (GQDs) with a particle size ranging from 5-10 nm embedded in polyethylene glycol (PEG) matrix with a particle size ranging from 80-100 nm, for drug delivery and biomedical applications.

In an embodiment of the present invention, the composition of PEG-GQD at a concentrations of about 8 mg/mL shows up to 50% cell viability when tested on HeLa cell lines.

In another embodiment, present invention provides a process for preparation of biocompatible composition comprising the steps of:
i. electrochemical etching of multi walled carbon nanotubes at temperature in the range of 25°-28° C. for period in the range of 11 to 12 hrs to provide graphene quantum dots of size 5-10 nm;
ii. mixing the graphene quantum dots as obtained in step (i) with polyethylene glycol followed by sonicating at temperature in the range of 20 to 35° C. for period in the range of 25 to 30 minutes to obtain a solution;
iii. autoclaving the solution as obtained in step (ii) at temperature in the range of 140°-180° C. for 23 to 24 hrs and;
iv. cooling at room temperature in the range of 20 to 35° C. followed by dialyzing to obtain biocompatible composition.

In yet another embodiment of the present invention, the concentration of GQDs embedded in polyethylene glycol is in the range of 1 mg/mL to 4 mg/mL.

BRIEF DESCRIPTION OF THE FIGURES

FIG. 5A The viability at 5.5 mg/ml is maximum for PEG-GQD compared to Crude-GQD and Hydro-GQD; FIG. 5B the viability at 8 mg/ml.

FIG. 6 depicts fluorescence microscopy images of HeLa cells incubated with GQDs imaged via DAPI (4′,6-diamidino-2-phenylindole) filters. Scale bars are 50 μm.

FIG. 7A through FIG. 7C depict: FIG. 7A shows ROS production in solution containing samples with 20 μM $H_2O_2$ at 0 and 90 min. FIG. 7B shows Intracellular ROS in HeLa cells. FIG. 7C shows Intracellular ROS imaged in HeLa cells. Green: DCF. Scale bar is 50 μm.

FIG. 8A through FIG. 8D depict: FIG. 8A shows Absorbance spectra and FIG. 8B shows Fluorescence spectra, of P-GQD-Dox, C-GQD-Dox and free Dox FIG. 8C shows HeLa cell viability after incubation with P-GQD-Dox & C-GQD-Dox. FIG. 8D shows Intracellular delivery of Dox with P-GQD-Dox. Red: Dox, Blue: GQDs. Scale bar is 50 μm.

FIG. 9A through FIG. 9C depict: Electron micrographs for hydrothermal treatment at various PEG concentrations. FIG. 9A shows 0.2 mg/mL (SEM). FIG. 9B shows 0.2 mg/mL (TEM). FIG. 9C shows 4 mg/mL (SEM).

FIG. 10B shows S-GQD (SEM) and FIG. 10C shows P-GQD (TEM).

FIG. 11A shows FTIR spectra for P-GQD, C-GQD and H-GQD. PEG and GQD signature peaks are shown by red and black arrows respectively. FIG. 11B shows PL and PLE spectra of GQDs.

FIG. 12: C1s XPS spectra of C-GQD, H-GQD and P-GQD indicating surface changes during the PEGylation process. The reduction of oxygenated functional groups in H-GQDs is indicated by the loss of C=O (288.5 eV) and C—O—C (287.2 eV) peaks in comparison with C-GQDs. P-GQDs show increase in —OH peak intensity due to hydroxyl group from PEG.

FIG. 13A through FIG. 13D depict: TEM images of FIG. 13A shows C-GQD, FIG. 13B shows H-GQD and FIG. 13C and FIG. 13D show P-GQDs. The individual GQDs in P-GQDs can clearly be seen at high resolution in FIG. 13D.

FIG. 14A through FIG. 14B depict: FIG. 14A shows Absorbance spectra of C-GQD, H-GQD and P-GQD with inset showing image of the GQD solution in water under white light and UV. The small peak at 270 nm due to GQDs can easily be identified. This peak was matched for all three samples for confirming the GQD concentrations. FIG. 14B shows Excitation dependent shift in the emission maxima for C-GQD, H-GQD and P-GQD. PLE spectrum at 424 nm emission for the three GQD samples is similar in shape showing no change in excitation, emission mechanism after hydrothermal treatment FIG. 15A through FIG. 15C depict: FIG. 15A shows Schematic representation of protein interaction study of GQDs with BSA. Polyacrylamide gel electrophoresis (PAGE) showing quantity of BSA in FIG. 15B supernatant and pellet for P-GQD, C-GQD and H-GQD; (BSA=4 mg/mL) and FIG. 15C in the supernatant and pellet for P-GQD, C-GQD, S-GQD and H-GQD; (BSA=0.4 mg/mL).

FIG. 16: Hela cell viability for C-GQD, S-GQD, H-GQD and P-GQD assessed by MTT assay.

FIG. 17B: Bar graph showing fluorescence values due to ROS production at 0 and 90 minutes for GQD+10 μM $H_2O_2$, clearly indicating the maximum increase in ROS for H-GQD+$H_2O_2$. P-GQD produced least ROS even after 90 minutes in presence of $H_2O_2$ and the levels were similar to that of without $H_2O_2$ samples.

FIG. 19A and FIG. 19B depict: Intracellular ROS generation in HeLa cells incubated with GQDs, visualized by fluorescence microscopy (Scale bar=50 μm, Magnification 40×). Green fluorescence is from DCF, a ROS detecting dye.

FIG. 20: Fluorescence microscopy images showing delivery of doxorubicin with P-GQD-Dox, H-GQD-Dox and C-GQD-Dox. Red: Dox, Blue: GQDs. (Scale bar=20 μm, Magnification 63×).

ABBREVIATIONS

Figure 1A:
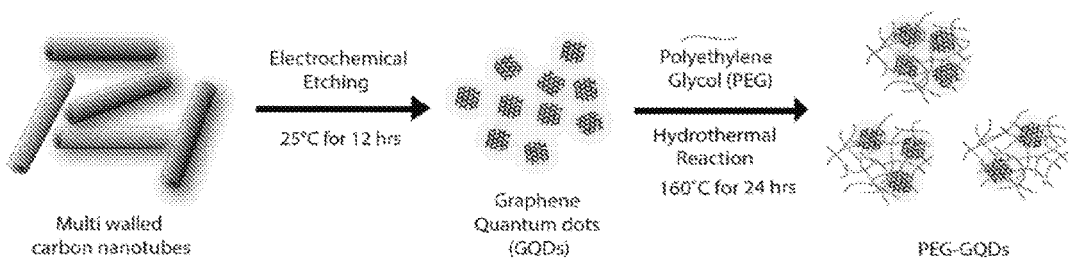
FIG. 1A represents the process for production of the biocompatible composition of GQD embedded in polymer matrix.

P-GQD: PEG embedded GQD
H-GQD: Hydrothermally treated GQD
S-GQD: GQD with PEG shell

DETAILED DESCRIPTION OF THE INVENTION

The present invention provides a biocompatible composition (PEG-GQDs) comprising Fluorescent Graphene Quantum Dots (GQDs) embedded in a polymer matrix of polyethylene glycol (PEG) with particle size ranging from 80-100 nm (The polymer matrix is consisting of PEG. The GQDs are embedded in PEG matrix. The PEG matrix size is unaffected by presence or absence of GQDs. The matrix formation is solely dependent on concentration of PEG used during hydrothermal step. Here the particle size refers to PEG matrix with GQDs embedded in it) for application in drug delivery, bioimaging and other biomedical applications.

The invention further provides a hydrothermal process to synthesize the GQD-PEG composition.

In another aspect the invention provides reduced cytotoxicity of the instant PEG-GQDs composition, wherein 50% cell viability is obtained at PEG-GQDs concentration of 8.0 mg/ml.

Accordingly, the PEG matrix aids in reducing the reactive oxygen radicals (ROS) generated by the GQD surface while keeping the small GQDs inside the matrix; thus, also reducing their undesirable interactions with cellular proteins and organelles.

The invention provides a process for preparation of PEG-GQDs composition comprising the following steps:
a) electrochemical etching of multi walled carbon nanotubes at 25°-28° C. for 11 to 12 hrs to provide graphene quantum dots of size 5-10 nm and;
b) subjecting the graphene quantum dots to hydrothermal reaction at 140°-180° C. for 23 to 24 hrs in the presence of polyethylene glycol to provide PEG-GQDs composition of size 80-100 nm.

The process for production of the biocompatible composition of GQD embedded in polymer matrix is described in scheme 1.

The PEG-GQD composition comprises GQDs nanoparticles with a particle size ranging from 5-10 nm embedded in a polymer matrix of size ranging from 80-100 nm.

The key feature of the invention involves a hydrothermal process, wherein several graphene quantum dots are arranged into a PEG particle. The resultant PEG-GQD composition comprises GQDs nanoparticles with particle size ranging from 5-10 nm embedded in a polymer matrix. The composition is a larger nanoparticle with a particle size ranging from 80-100 nm. Particle size characterization by Transmission Electron Microscopy (TEM) indicates that the GQDs do not aggregate in the polymer matrix.

The invention provides characterization of the instant biocompatible composition by using analytical techniques including UV-visible spectrophotometry, Fluorescence spectrophotometry, Fourier Transform infrared spectroscopy (FTIR) and Transmission Electron microscopy (TEM) to indicate that the graphene quantum dots in the instant biocompatible composition retain their fluorescent properties and their characteristic particle size even after PEGylation by the hydrothermal process.

The characterization processes are performed for crude-GQDs and hydro-GQDs (GQDs hydrothermally treated without PEG) as controls to compare their properties with PEG-GQDs.

In standard conditions, the UV spectrum of graphene oxide/reduced graphene oxide has an absorption peak ranging from 230-270 nm. The UV absorbance of the instant PEG-GQD composition is retained at 270 nm. (Refer FIG. 1)

Figure 2:
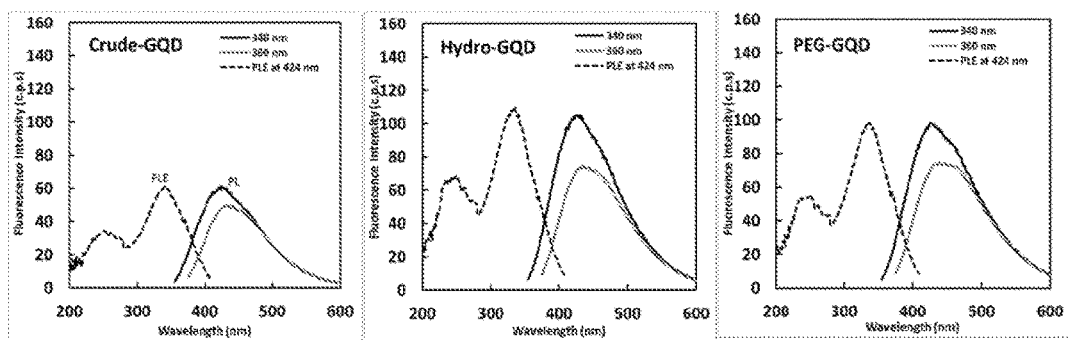
FIG. 2 depicts the photoluminescence spectra and photoluminescence excitation spectra of crude-GQD, hydro-GQD and PEG-GQD.

The Photoluminescence Excitation Spectra (PLE) at 424 nm exhibits the excitation maxima for the crude-GQDs, hydro-GQDs (without PEG) and PEG-GQDs. (Refer FIG. 2) FTIR spectroscopy confirms the PEGylation process of the GQDs.

These techniques indicate that the graphene quantum dots in the instant biocompatible composition retain their fluorescent properties and their characteristic particle size after PEGylation by the hydrothermal process.

The invention provides biocompatible composition with ROS quenching ability and thus reduces the cytotoxicity even at higher concentrations.

Drug delivery capability of P-GQDs in comparison with unmodified GQDs is disclosed. The HeLa cell viability of P-GQD-Dox (doxorubicin), was around 26% whereas for C-GQD-Dox it was ~58% (FIG. 8C), which indicates the remarkable ability of P-GQDs to load more Dox and efficiently deliver it in HeLa cells.

Further, toxicity of the PEG-GQDs composition is assessed using the MTT assay. The cellular uptake of PEG-GQDs by HeLa cell lines is detected by Fluorescence microscopy.

Figure 5A:
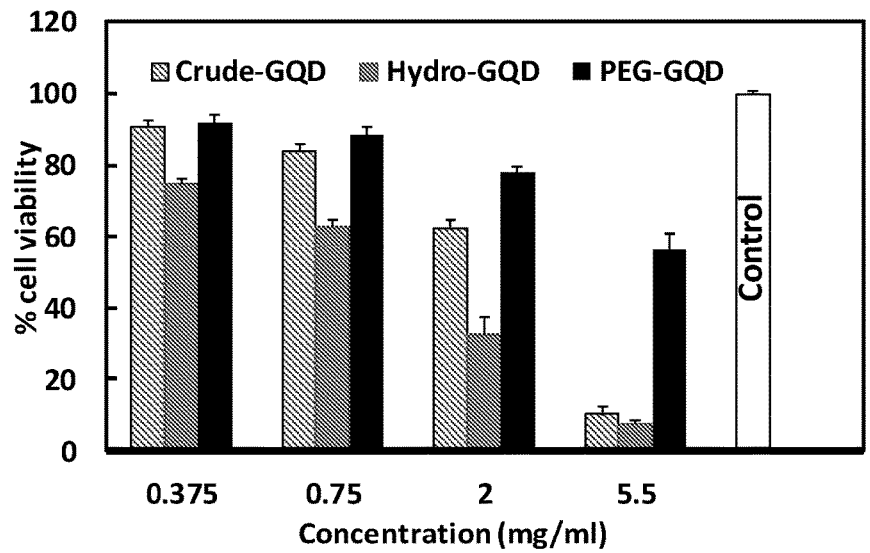
FIG. 5A and FIG. 5B depict the % cell viability of HeLa cells by normalized MTT (3-(4,5-dimethylthiazol-2-yl)-2,5-diphenyltetrazolium bromide) assay for Crude, Hydro and PEG-GQDs. The difference in viability for the three GQDs increases as concentration increases.

Accordingly, the effect of the GQDs concentration on HeLa cell lines is determined by the MTT assay. At PEG-GQD concentrations of 5.5 mg/ml, 60% cell viability was obtained, whereas crude-GQDs and hydro GQDs (without PEG) at the same concentration of 5.5 mg/ml have cell viability of 10-15% (FIG. 5A).

Further, pegylated GQDs were easily assimilated/taken up by HeLa cells as indicated by fluorescence microscopy images after 4 h incubation of pegylated GQDs with HeLa cells (FIG. 6).

EXAMPLES

Following examples are given by way of illustration and therefore should not be construed to limit the scope of the invention.

EXAMPLE 1

UV-Vis Absorbance Characterization

Figure 1B:
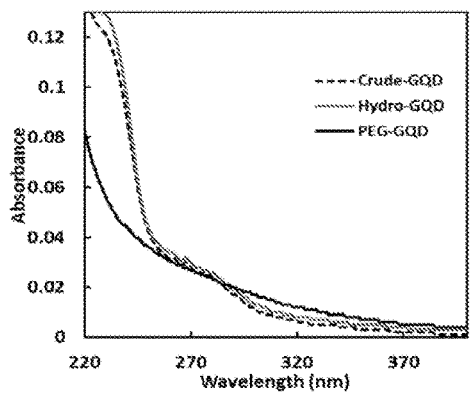
FIG. 1B depicts the UV absorbance spectra of crude-GQD (C-GQD), hydro-GQD and PEG-GQD.

The characterization was done to investigate the effect of PEGylation on different properties of GQDs. UV absorbance was measured and compared at 270 nm for obtaining the concentration of Crude-GQD, Hydrothermally treated GQD without PEG (hydro-GQD) and PEG-GQD (FIG. 1). The three types of GQDs exhibited approximately equivalent values of absorbance at 270 nm.

EXAMPLE 2

Luminescence Property Characterization

Fluorescence spectrum was collected using various excitation wavelengths (340 nm, 360 nm), to observe any changes in the emission intensity of the GQDs after PEGylation. As observed from the spectra in FIG. 2, the fluorescence emission intensity and emission maxima position was maintained after PEGylation. The PLE (Photoluminescence) spectra at 424 nm exhibited excitation maxima for crude-GQD, Hydro-GQD and PEG-GQD which suggested no variation in the photoluminescence properties of the GQDs after the PEGylation process. Thus, one can conclude that the luminescence properties of the GQDs are maintained after PEGylation.

EXAMPLE 3

PEG Characterization

FTIR spectroscopy (FIG. 3) was used to confirm PEGylation process. The arrows in FIG. 3 indicated the peak positions, which are signature of PEG. The presence of peaks for PEG as well as GQDs in PEG-GQD spectra confirmed the PEGylation of the GQDs.

EXAMPLE 4

Size Characterization

The size of the GQDs was characterized by transmission electron microscopy (TEM). As observed from TEM images (FIG. 4), crude-GQDs were about 5-10 nm and PEGylation resulted in approximately 80 nm polymer particles with GQDs embedded in them. Higher resolution TEM images clearly indicated that the GQDs have not aggregated in the polymer matrix. There was no change in size due to the hydrothermal treatment without PEG.

EXAMPLE 5

Process for Preparation of GQDs

Graphene quantum dots (GQDs) were synthesized from Multiwalled carbon nanotubes (MWCNTs) via the application of a controlled interfacial electric field as reported elsewhere.[1] In brief, a suspension of MWCNT (2 mg/mL) was prepared in N, N-dimethyl formamide (DMF), and drop casted on platinum electrode followed by thorough drying under IR lamp. Three such layers were casted and a positive bias of 3 V was applied to MWCNT coated electrode in acetonitrile containing 0.1 M TBAP for 12 h. It was followed by reduction in the same electrolyte at −2 V for ~4 h. The average diameter (lateral size from TEM) after all post-synthetic treatments was 6.6±0.7 nm. The organic solvent was removed using rota vapor, the dried GQDs along with salt were dissolved in deionised (DI) water and centrifuged at 2880 g for 5 minutes to precipitate out the salts, which were sparingly soluble in water. The supernatant was further dialyzed using 3.5 kDa cut-off dialysis tubing for 4 h with replacement of water every hour to remove remaining traces of salt.

EXAMPLE 6

Process for Preparation of PEG Embedded GQD

To optimize the size of PEG matrix formed during PEGylation of GQDs, various concentration of PEG (4, 2 and 0.2 mg/mL) was prepared and heated hydrothermally in Teflon lined stainless steel autoclave for 24 h. After the hydrothermal treatment the solution obtained was dialyzed using 10 kDa cutoff dialysis tubing against deionized water. The concentration of PEG yielding a larger particle after hydrothermal treatment was selected for PEGylation of GQDs.

The electrochemically prepared GQDs were PEGylated using a hydrothermal process in which 20 mg PEG (8 kDa) was mixed in 5 mL of GQDs and sonicated for 30 minutes at room temperature. The solution was then sealed in Teflon lined 25 mL stainless steel autoclave and heated at 160° C. for 24 h. After 24 h the autoclave was cooled at room temperature. The solution was dialyzed using 10 kDa cut off dialysis tubing to remove unreacted free PEG. GQDs thus obtained were denoted as P-GQDs (PEG-GQDs).

EXAMPLE 7

Synthesis of C-GQD; P-GQD; S-GQD and H-GQD

The GQDs were synthesized by electrochemical unzipping of multiwalled carbon nanotubes (MWCNTs) as per a slightly modified recently reported method (*Chem.-Eur. J.* 2012, 18, 12522-12528). This electrochemical procedure provides good control over size and shape of the GQDs and yields of GQDs without any toxic by-products. The synthesis was carried at room temperature (27° C.), by application of an interfacial electric field for oxidation followed by reduction of the MWCNTs. The water soluble crude-GQDs (C-GQDs), thus obtained, were PEGylated, to form PEG nanoparticles with GQDs embedded in them (P-GQDs). The PEGylation was performed by optimizing the concentration of PEG to yield ~100 nm matrix rather than coating single GQDs with a shell, which would yield <20 nm particles. At higher concentration of PEG (4 mg/mL), large ~80-100 nm spherical particles were observed due to the hydrothermal polymerization (*Biotechnol. Biofuels* 2013, 6, 15) whereas, at lower concentration such big polymeric assemblies were not observed. The variation in concentration was used to obtain GQDs with either a PEG shell (S-GQDs) or embedded in a PEG matrix (P-GQDs) (FIG. 10). The hydrothermal reaction of GQDs with PEG (MW 8 kDa) was carried out at 160° C. in an autoclave. After 24 h, the solution obtained was dialyzed to remove unreacted PEG, yielding P-GQDs. A similar hydrothermal protocol was followed without PEG to obtain hydrothermally treated-GQDs (H-GQDs), which were used as control sample for studying the effect of hydrothermal treatment, on GQD's. For investigating the effect of embedding GQDs into PEG matrix in comparison to coating with a polymer shell, S-GQDs were synthesized, (GQDs with a PEG shell), via a similar hydrothermal treatment but with less concentration 0.2 mg/mL of PEG.

EXAMPLE 8

FTIR Characterization of P-GQDs

Figure 3:
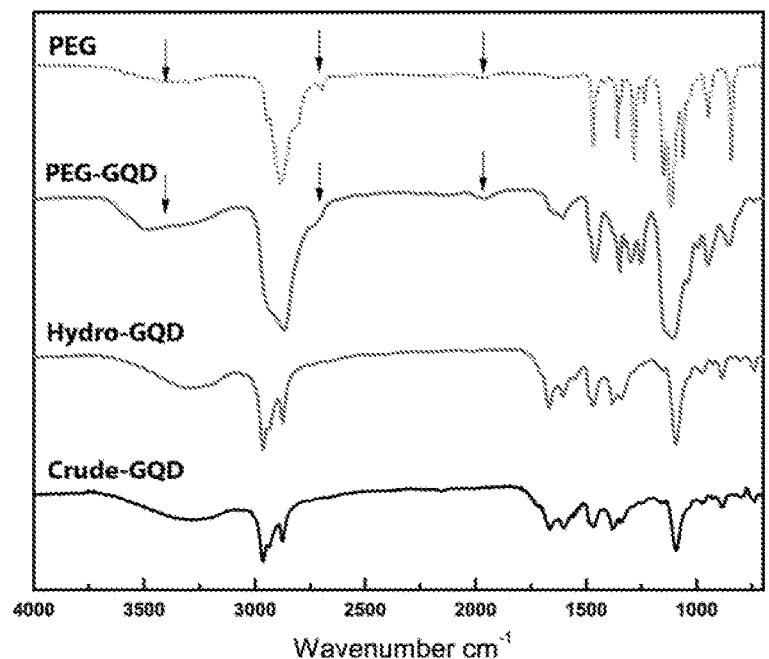
FIG. 3 depicts FTIR (Fourier Transform infrared spectroscopy) spectra exhibiting PEGylation of GQD compared to crude GQD and hydrothermal GQD, the PEG signature peaks are indicated by arrows.

The PEGylation of GQDs was characterized by Fourier transform infrared spectroscopy (FTIR). The FTIR spectra for C-GQDs, free PEG, H-GQDs and P-GQDs are shown in FIG. 3. The C-GQDs and H-GQDs both showed the presence of alkane C—H, C═C, and O—H vibrations. The P-GQDs showed the presence of both PEG and GQD signature peaks at 2880 $cm^{-1}$ and 1640 $cm^{-1}$. In addition, the P-GQDs also show peaks around 2950 $cm^{-1}$ and 3460 $cm^{-1}$ corresponding to the C—H stretch from GQDs and O—H stretch from the PEG respectively. PEGylation is also confirmed by X-ray photoelectron spectroscopy (XPS) of the C1s level in GQD samples before and after PEGylation (FIG. 12). The C—C (284.4 eV), C—OH (285.7 eV), and C—O (286.6 eV) binding energy peaks were observed in all the samples. However, the C—OH (285.7 eV) peak was significantly higher for P-GQDs as compared to C-GQDs and H-GQDs, as attributable to some unreacted —OH groups from PEG and hydroxyl groups from the GQD surface. The hydrothermal process is known to reduce oxygenated functional groups such as carboxylic acid, epoxy, alkoxy, and carbonyl present on the C-GQD surface to hydroxyl (*Adv. Mater.* 2010, 22, 734-738). This was indicated by the loss of C═O (288.5 eV) and C—O—C (287.2 eV) peaks in H-GQD compared to C-GQDs.

EXAMPLE 9

TEM Characterization of GQDs

Figures 4A, 4B:
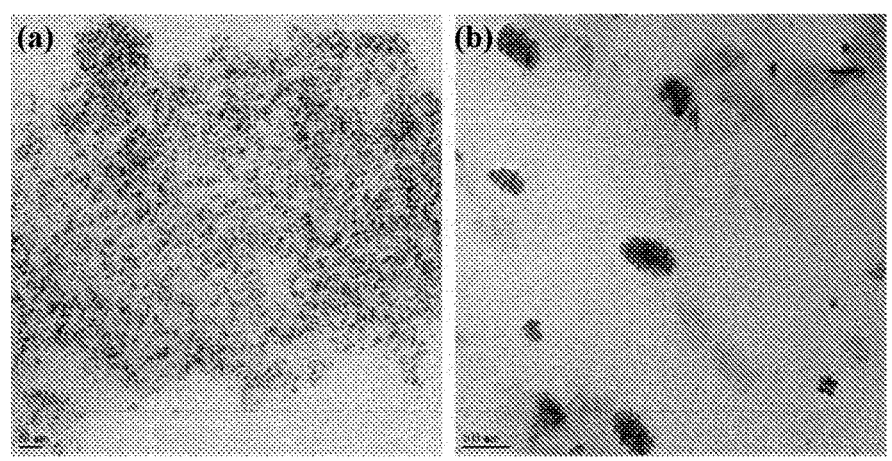
FIG. 4A and FIG. 4B depict Transmission Electron Microscopy Images wherein FIG. 4A crude GQDs exhibit monodispersed nanoparticles and FIG. 4B PEG-GQD composition indicates single GQDs embedded in a matrix.
Figures 10A, 10B, 10C:
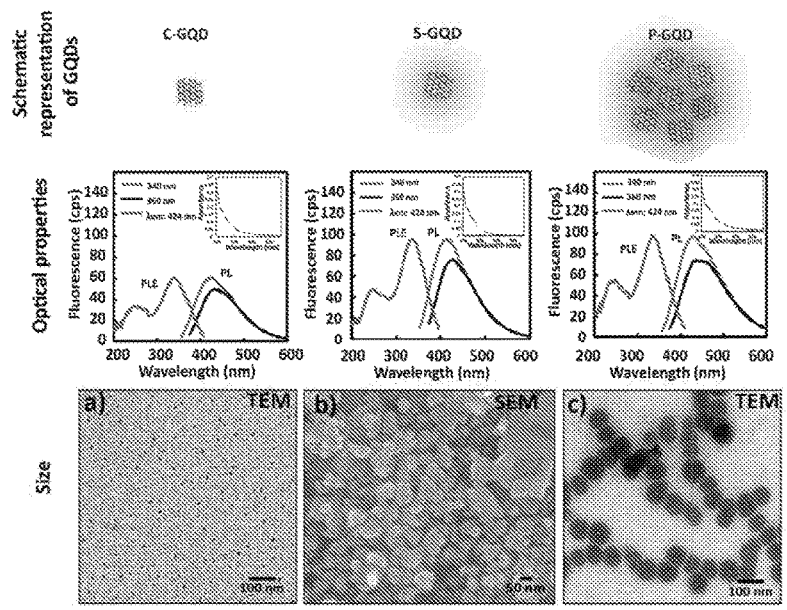
FIG. 10A through FIG. 10C depict: Optical and size characterization for unmodified GQDs (C-GQDs). Single PEG shell coated GQDs (S-GQDs) and matrix embedded GQDs (P-GQDs). Electron micrographs for FIG. 10A shows C-GQD (TEM)

The morphology and size of the GQDs were characterized by Transmission Electron Microscopy (TEM) and Atomic Force Microscopy (AFM). The average diameter of C-GQDs was found to be 6.6±0.7 nm, indicating a narrow dispersion (FIG. 4, FIG. 13A). The topographic height was observed to be ~1-2 nm (FIG. 13E). The hydrothermal treatment does not aggregate or change the size of the GQDs (FIG. 13B): the average size of H-GQDs was similar to C-GQDs. The PEGylation process yielded 88±18 nm nanoparticles consisting of individual GQDs embedded in a PEG matrix (FIG. 4 and FIG. 13C and FIG. 13D). The size of GQDs inside the PEG matrix remained unaltered (FIG. 13D) indicating no adverse effect of the PEGylation process on GQD size. A lower concentration of PEG resulted in smaller sized nanoparticles (38±6 nm). S-GQDs, which are GQDs coated with a PEG shell (FIG. 10B).

EXAMPLE 10

UV-Vis Absorption and Photoluminescence (PL) Characterization of GQDs

Figures 11A, 11B:
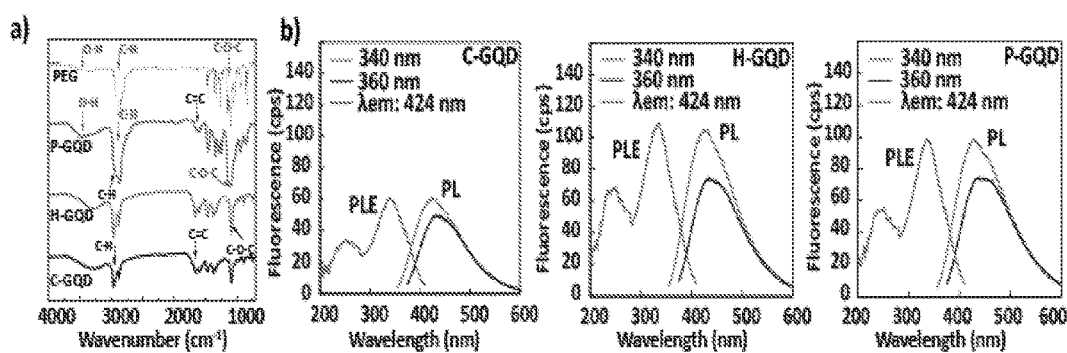
FIG. 11A through FIG. 11B depict.

The quantum yield of the GQDs was estimated to be ~3-4%, which is comparable to graphene based bio imaging probes used in the literature (*Phys. Chem. Chem. Phys.* 2013, 15, 19013-19018). Interestingly, the hydrothermal treatment and PEGylation process did not affect the quantum yield (Table S1). The UV-Vis absorption spectra of C-GQDs, H-GQDs, S-GQDs and P-GQDs were similar with a broad absorption band at ~270 nm (FIG. 10 and FIG. 14A). The PL spectrum (FIG. 10, FIG. 11B and FIG. 14B) for C-GQDs, H-GQDs, S-GQDs and P-GQDs showed the characteristic excitation-dependent PL behavior of GQDs with a broad peak around 420 nm (*Eur. J.* 2012, 18, 12522-12528). Photoluminescence excitation (PLE) spectra for GQDs before and after PEGylation were also similar, with two distinct peaks at 240 nm and 330 nm. Thus, it confirmed that the PEGylationPEGylation does not adversely affect the optical properties of GQDs, making them useful for bioimaging.

TABLE S1

Quantum yields for GQDs with Quinine hemisulphate as reference.

| Sample | Quantum Yield (%) |
|---|---|
| C-GQD | 2.55 |
| H-GQD | 4 |
| P-GQD | 2.85 |

EXAMPLE 11

Protein-GQD Interaction Assay

The effect of PEGylationPEGylation on non-specific protein interaction of GQDs via a protein-GQD interaction assay (FIG. 15A) was assessed by the inventors. The C-GQDs, H-GQDs, S-GQDs and P-GQDs were incubated with BSA solution at 37° C. for 2 h. After the interaction with proteins the aggregated GQD-protein can be pelleted out easily by centrifugation. The samples were thus centrifuged and the pellet and supernatant ran over a gel to analyze the presence of proteins. As can be seen from FIG. 15B and FIG. 15C, P-GQDs had the least interaction with the protein as indicated by less protein in the pellet and more protein in the supernatant. S-GQDs also showed less protein in the pellet compared to C-GQDs and H-GQDs confirming the ability of PEG to resist protein interaction. On the other hand, for C-GQDs and H-GQDs more protein was observed in the pellet, compared to the supernatant (FIG. 15B). These results confirmed that smaller sized GQDs without PEG interacted with proteins the most, followed by smaller sized PEG coated GQDs (S-GQDs), compared to the GQDs embedded in PEG matrix.

EXAMPLE 12

Toxicity Assay and Cell Imaging

The cytotoxicity due to the GQDs were assessed using MTT assay (FIG. 13A), which is a colorimetric assay to measure the mitochondrial activity that reflects the population of viable cells present. HeLa cells were cultured in a 96 well plate for 12 h at a density of $10^4$ cells per well. Different concentrations of the Crude-GQD, Hydro-GQDs and PEG-GQDs were added to the wells and the cells were incubated for 24 h at 37° C. Reduced toxicity was observed for PEG-GQD sample compared to Crude-GQDs and Hydro-GQDs (FIG. 5A). The effect of concentration on the cytotoxicity was more prominent at higher concentrations. At about 5.5 mg/ml concentration of GQDs, almost 60% cells were viable for PEG-GQDs whereas only 5-10% were viable for Crude-GQDs and Hydro-GQDs. All the values were normalized w.r.t blank reading, which involved cells without any treatment showing maximum cell viability.

Figure 5B:
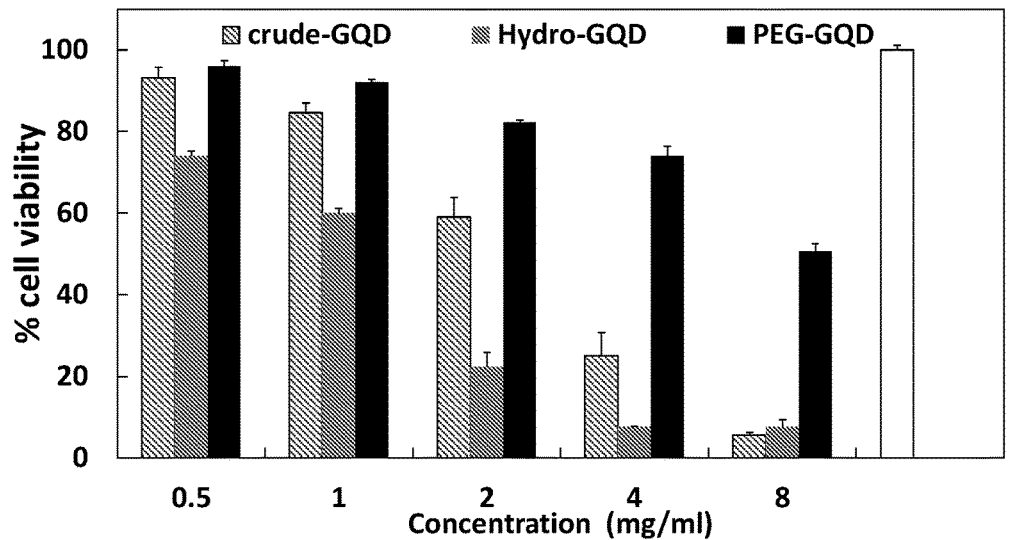

Further the HeLa cells were incubated with various concentrations of C-GQDs, H-GQDs, S-GQDs and P-GQDs for 24 h after which the cytotoxicity was quantified by dissolving the formazan crystals formed by the live cells and measuring the absorbance at 550 nm. No significant toxicity was observed at GQD concentrations lower than 0.4 mg/mL. At concentrations higher than 0.4 mg/mL, C-GQDs and H-GQDs showed more toxicity than P-GQDs (FIG. 5B). The P-GQDs did not show any significant cellular toxicity. At about 4 mg/mL, almost 75% cells were viable for P-GQDs whereas only 25% and 5% cells were viable for C-GQDs and H-GQDs respectively. This data suggests that indeed the PEGylation process has made the GQDs less cytotoxic. The excellent cell viability due to P-GQDs was maintained even at a very high concentration. About 50% cells were found viable at ~8 mg/mL. This low cytotoxicity at such high concentrations has not been reported till date. Interestingly, when compared with S-GQDs, P-GQDs were well tolerated even at 4 times higher concentration (FIG. 16). S-GQDs showed about 70% and 20% cell viability at 2 mg/mL and 4 mg/mL respectively. Thus, confirming that embedding the GQDs in a matrix might reduce the cytotoxicity.

After confirming the improved biocompatibility of P-GQDs vis a vis unmodified GQDs, the same were evaluated for its potential application in bio-imaging. The HeLa cells with C-GQDs, H-GQDs, and P-GQDs were incubated. As can be seen from fluorescence microscopy images (FIG. 6), all GQDs including P-GQDs, were easily internalized into the cells after 4 h of incubation. A strong blue fluorescence from the cell cytoplasm was observed for cells incubated with GQDs, compared to the cells without any GQDs. Thus, the cytotoxicity data and uptake experiment together indicate that P-GQDs can be used for cell imaging without adverse cytotoxic effects at higher concentrations (above 1 mg/mL), unlike unmodified GQDs, which are relatively toxic at those concentrations.

EXAMPLE 13

Cellular Uptake of GQDs

HeLa cells were plated on 12 mm cover slips in a 24 well plate at a density of $3\times10^4$ cells per well for 12 h. Each of the treated GQDs, i.e. Crude-GQDs, Hydro-GQDs and PEG-GQDs at concentrations of 3 mg/ml were added to wells. The cells were further incubated for 4 h. Post the incubation period, the media was removed and cells were washed three times with Dulbecco's Phosphate Buffered Saline (DPBS). The cells were then fixed using 2% paraformaldehyde fixation buffer (PFA) for 30 mins and washed three times with DPBS. Finally the cover slips were removed and mounted on microscopy slides and imaged using fluorescence microscope using UV excitation and DAPI filters. The cells with GQDs fluoresced blue while no fluorescence was observed in control (without GQDs) samples. The pegylated GQDs were easily taken up by HeLa cells as indicated by the fluorescence images after incubation of the GQDs for 4 h (FIG. 6).

EXAMPLE 14

ROS Quenching Ability of PEG-GQDs

Figure 17A:
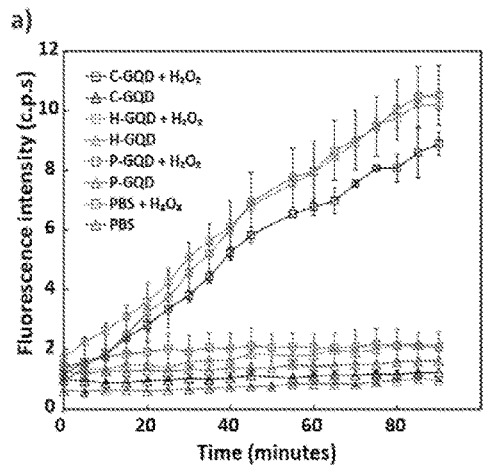
FIG. 17A and FIG. 17B: Cell free ROS assay for GQDs in presence of FIG. 17A 10 μM $H_2O_2$ showing fluorescence intensity at different time points over 90 minutes at 37° C. GQDs without $H_2O_2$ were taken as negative control. There was minimum fluorescence increase for P-GQD sample indicating less ROS production.
Figure 17B:
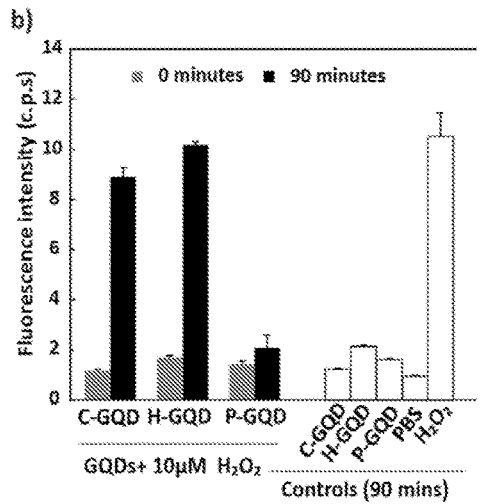
Figure 18A:
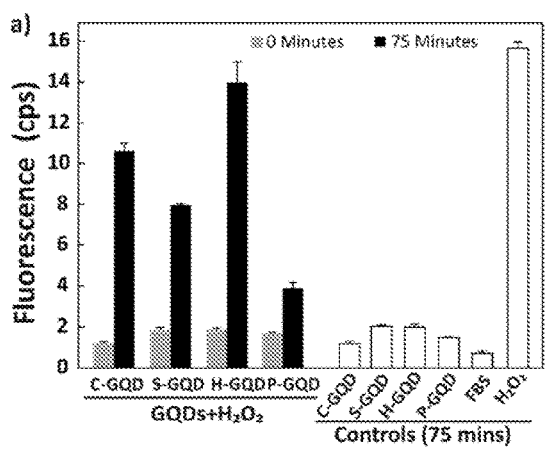
FIG. 18A: Fluorescence intensities for cell free ROS assay after 0 and 75 minutes of incubation of GQDs with 20 μM $H_2O_2$. After 75 minutes, P-GQDs showed very less ROS production compared to C-GQD, S-GQD and H-GQD. S-GQDs showed ROS production lower than C-GQDs but higher than P-GQDs.
Figure 18B:
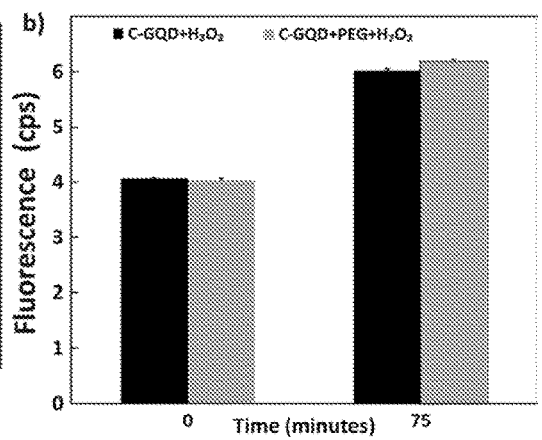
FIG. 18B: Effect on ROS production due to presence of free PEG in the solution along with C-GQD. No significant quenching is observed.

The samples (C-GQDs, H-GQDs, S-GQDs and P-GQDs) were incubated with $H_2O_2$ in 10% fetal bovine serum (FBS) solution at 37° C. Chemically hydrolyzed 2,7-dichlorodihydrofluorescein diacetate ($H_2$DCF-DA), yielding $H_2$DCF, was used as a fluorescent indicator of ROS production. The increase in ROS over 90 min with 10 µM and 20 µM $H_2O_2$ in the presence and absence of GQDs were monitored. In the case of C-GQDs and H-GQDs incubated with 20 µM $H_2O_2$, the ROS production increased ~3 and ~4 times respectively (FIG. 7A). This was in contrast to P-GQDs, where there was no significant increase in ROS over 90 min. For a lower concentration of $H_2O_2$ (10 µM), there was no increase in ROS when incubated with P-GQDs (FIG. 17), which indicates that the PEG matrix was able to quench even the ROS produced by $H_2O_2$. A similar but less pronounced quenching was observed for the S-GQDs (FIG. 18A). Thus, confirming again the ROS quenching ability of PEG. However, adding free PEG to C-GQDs did not quench the ROS produced in solution (FIG. 18B). Interestingly, more quenching was observed in P-GQDs compared to the S-GQDs suggesting the ability of a thicker PEG matrix to quench ROS more effectively. C-GQDs and H-GQDs with 10 µM $H_2O_2$ showed significantly higher ROS production (FIG. 17). The H-GQDs produced more ROS than C-GQDs, likely because of more free-radical-susceptible hydroxyl groups on the surface generated by the hydrothermal treatment.

Further the inventors examined intracellular ROS produced, when HeLa cells were incubated with GQDs. HeLa cells were first incubated with 15 µM $H_2$DCF-DA dye for 1 h followed by incubation with 2 mg/mL GQDs for 6 h. The acetate groups on the non-fluorescent $H_2$DCF-DA were cleaved by intracellular esterases and further oxidation due to ROS converts $H_2$DCF to a highly fluorescent 2,7-dichlorofluorescein (DCF). As can be seen from FIGS. 7B and FIG. 19, P-GQDs showed lower intracellular ROS levels compared to H-GQDs, which showed the highest levels of ROS. The intracellular ROS produced by the GQDs by imaging cells incubated with dye and GQDs was also evaluated. The cells incubated with H-GQDs showed highest green fluorescence due to ROS formation. The C-GQDs showed little green fluorescence (FIG. 19A and FIG. 19B) suggesting low but slightly more ROS production compared to cells without any GQDs. On the other hand, P-GQDs showed almost no fluorescence (FIG. 7C and FIG. 19). Thus, both quantitative fluorescence measurement as well as cell imaging showed less ROS production for P-GQDs as compared to H-GQDs. This emphasizes the ability of PEG matrix to lower the intracellular ROS production usually observed when cells are treated with GQDs. These results indicate the role of ROS production in the high toxicity exhibited by H-GQDs and also the ability of PEG matrix to mitigate this ROS-caused toxicity.

It is noteworthy that the high doses of drugs can be delivered safely by P-GQDs as it can be tolerated at significantly higher concentrations. In addition, the PEG matrix can load more drug than the unmodified GQD surface.

EXAMPLE 15

Drug Delivery Capability of P-GQDs in Comparison with Unmodified GQDs

For drug loading, C-GQDs and P-GQDs were lyophilized and soaked in doxorubicin (Dox), a chemotherapeutic, solution for 30 min, followed by purification by dialysis. The Dox loading was estimated by measuring the Dox absorbance. For P-GQDs, about twice the amount of Dox was loaded compared to C-GQDs (FIG. 8A). The fluorescence of GQDs was also unaffected by Dox loading as indicated by the spectra in FIG. 8B, where fluorescence due to both GQDs and Dox can be observed in P-GQD-Dox.

To test cytotoxic effect of Dox-loaded GQD, 4 µg/mL of C-GQD-Dox and P-GQD-Dox, containing 0.1 µM and 0.2 µM Dox respectively were incubated with HeLa cells. Consequently, the cell viability was assessed after 48 h using the MTT assay. For P-GQD-Dox, cell viability was around 26% whereas for C-GQD-Dox it was ~58% (FIG. 8C). More significantly, no toxicity was observed in C-GQDs and P-GQDs without Dox. These results clearly indicate the remarkable ability of P-GQDs to load more Dox and efficiently deliver it in HeLa cells.

Dox and GQD fluorescence was used for imaging the cells after the GQDs were internalized. Accordingly, FIG. 8D shows images of HeLa cells incubated with C-GQD-Dox, H-GQD-Dox and P-GQD-Dox. All GQD samples showed strong blue fluorescence in the cytoplasm of the cells compared to control cells (without GQDs). However, only the P-GQD-Dox had both red and blue fluorescence due to Dox and GQDs respectively. The Dox appeared to be localized in the nucleus of the cells, whereas GQDs were present in the cytoplasm (FIG. 20). These, results demonstrate that the P-GQDs can deliver Dox at higher concentrations as compared to C-GQDs. Thus, P-GQDs can provide a platform for delivering chemotherapeutics more efficiently along with enabling intracellular imaging.

In a nut shell, a simple method for mitigating cytotoxicity of GQDs is disclosed herein. By encapsulating well defined GQDs in a PEG nanoparticle, their cytotoxicity was greatly reduced. The unprecedented low cytotoxicity may be attributed to the ability of PEGylated GQDs to produce less intracellular ROS. The strategy employed here thus offers a platform for developing theranostic probes and will help in expanding the use of GQDs in biomedicine.

Advantages of Invention

Simple process of coating
GQDs formed biocompatible

We claim:
1. Biocompatible composition with reduced cytotoxicity comprising graphene quantum dots (GQDs) with a particle size ranging from 5-10 nm embedded in polyethylene glycol (PEG) matrix with a particle size ranging from 80-100 nm, for drug delivery and biomedical applications.

2. The biocompatible composition as claimed in claim 1, wherein the composition of PEG-GQD at a concentrations of about 8 mg/mL shows up to 50% cell viability when tested on HeLa cell lines.

3. A process for preparation of biocompatible composition as claimed in claim 1 comprising the steps of:
  i. electrochemical etching of multi walled carbon nanotubes at temperature in the range of 25°-28° C. for period in the range of 11 to 12 hrs to provide graphene quantum dots of size 5-10 nm;
  ii. mixing graphene quantum dots as obtained in step (i) with polyethylene glycol followed by sonicating at temperature in the range of 20 to 35° C. for period in the range of 25 to 30 minutes to obtain a solution;
  iii. autoclaving the solution as obtained in step (ii) at temperature in the range of 140°-180° C. for 23 to 24 hrs and;
  iv. cooling at room temperature in the range of 20 to 35° C. followed by dialyzing to obtain biocompatible composition.

4. The process as claimed in claim 3, wherein the concentration of GQDs embedded in polyethylene glycol is in the range of 1 mg/mL to 4 mg/mL.

* * * * *